United States Patent [19]

Pierson

[11] Patent Number: 4,468,271
[45] Date of Patent: Aug. 28, 1984

[54] METHOD OF MAKING A DEVICE FOR DETERMINING ANALYTE ACTIVITY

[75] Inventor: Charles W. Pierson, Rochester, N.Y.

[73] Assignee: Eastman Kodak Company, Rochester, N.Y.

[21] Appl. No.: 437,221

[22] Filed: Oct. 28, 1982

[51] Int. Cl.³ .................... B32B 31/18; B32B 31/20; G01N 27/30

[52] U.S. Cl. .................... 156/220; 156/229; 156/253; 204/416; 204/418; 204/419; 204/420; 422/58

[58] Field of Search ............... 204/416, 418, 419, 420, 204/400; 422/50, 58, 68; 156/229, 250, 253, 220; 29/592 R

[56] References Cited

U.S. PATENT DOCUMENTS 4,053,381  10/1977  Hamblen et al. ............... 204/416
4,184,936  1/1980   Paul et al. ..................... 204/400
4,336,091  6/1982   Gottermeier ................ 156/244.12

Primary Examiner—G. L. Kaplan
Attorney, Agent, or Firm—Milton S. Sales

[57] ABSTRACT

A device is disclosed for determining the ionic analyte activity in liquids, e.g. aqueous solutions, by the use of electrodes and an internal capillary bridge which promotes ionic migration between the electrodes. This device includes an electrically insulative frame in which the electrodes are mounted, liquid access holes aligned with the electrodes on a capillary bridge formed of a porous material, and a cover sheet element formed of a nonporous cover sheet. The cover sheet element extends over the electrodes and encapsulates the elongated capillary bridge. Located in the cover sheet directly over and generally along the capillary bridge is one or more substantially continuous stretch lines typically provided by mechanically deforming the cover sheet. This deformation allows shorter junction times when liquids are introduced into the liquid access holes.

3 Claims, 14 Drawing Figures

METHOD OF MAKING A DEVICE FOR DETERMINING ANALYTE ACTIVITY

FIELD OF THE INVENTION

This invention relates to devices useful in determining the activity of an ionic analyte of a liquid, particularly by potentiometrically measuring ionic activity in drops of aqueous solutions, e.g. biological fluids.

BACKGROUND OF THE INVENTION

One device for measuring ionic activity in liquids is described in commonly assigned U.S. Pat. No. 4,184,936 (issued Jan. 22, 1980 to Paul et al). This device includes two ion-selective, solid electrodes mounted on a frame and a capillary bridge which promotes ionic migration between the two electrodes. The capillary bridge includes a nonporous support layer, a nonporous top layer and a porous layer therebetween. A pair of holes through the bridge and aligned with the electrodes allow liquid access to both electrodes. When a drop of reference solution of known ionic activity is applied to one fluid access hole and a drop of test solution of unknown ionic activity is applied to the other fluid access hole, the drops spread into the porous layer until contact is made at a thin junction interface, permitting ionic migration between the drops. The time it takes for the drops to spread adequately to form the thin junction interface and to allow ionic migration is termed the "junction time." An electrometer can be used to measure the electrical potential at the interfaces between each solution drop and its associated electrode to provide an indication of ionic activity in the test solution.

In commonly assigned U.S. Pat. No. 4,336,091 (issued June 22, 1982 to Gottermeier), an improved analyte activity measuring device and method of making same are described. The described device comprises two electrodes held in a frame by an integral cover sheet and capillary bridge. The cover sheet is formed of a nonporous material with an encapsulated porous ribbon, and fluid access holes extend through the cover sheet in alignment with the porous ribbon and each electrode. The test and reference fluids are confined to free spaces within the porous ribbon to form an ion junction between the electrodes.

The method of making the devices of the Gottermeier patent allows for improved manufacturing efficiencies in several respects. In this manufacturing method, however, the porous ribbon through which test and reference liquids travel is highly compressed in the encapsulation step. Typically, this porous ribbon is a porous paper composed of cellulosic fibers. When the paper is wetted with liquid samples, the cellulosic fibers swell, thereby reducing the free space in the ribbon even more. As a result, travel of the liquid samples within the ribbon is severely restricted and junction time is long.

Long junction times are highly undesirable in the health care field for both medical and economic reasons. Health care practitioners desire rapid analyses of biological fluids in an effort to render prompt medical diagnosis. Health care administrators desire to use highly automated analytical equipment at the most efficient rates of operation. Differences in junction time of only a few seconds, multiplied by the thousands of analytical tests made daily, can frustrate both desires.

Hence, there is a need in the art for a device useful in measuring ionic activity in liquids, which device has reduced junction time.

SUMMARY OF THE INVENTION

In accordance with a preferred embodiment of this invention, a device for determining the ionic analyte activity in a contacting sample of a test liquid with a contacting sample of a reference liquid comprises an electrically insulative frame and a pair of solid electrodes mounted in a spaced-apart relationship on a surface of the frame. Such device also includes a cover sheet element which extends over both of the electrodes. This element includes a cover sheet formed of a nonporous material and is bonded to the frame with the electrodes therebetween. A pair of liquid access holes having a common centerline extend through the cover sheet for receiving the liquid samples into contact with the electrodes. Each of such holes is aligned with a different electrode. The device further includes a capillary bridge formed of a porous material which is encapsulated in the cover sheet. This bridge has the directionality of the common centerline and extends at least between the liquid access holes for providing ionic flow of the liquid samples received in the holes. One or more substantially continuous stretch lines are located in the cover sheet directly over the capillary bridge extending generally along the common centerline in spaced relationship therewith.

A method for making the device described above includes encapsulating a ribbon of porous material in a nonporous cover sheet to form a cover sheet element. A pair of solid electrodes are applied to an electrically insulative frame member in a spaced-apart relationship. A pair of liquid access holes are then formed in the cover sheet element through the porous material, such liquid access holes having a common centerline. The cover sheet element is joined to the frame member with the electrode therebetween in an orientation such that each of the liquid access holes is aligned with a different electrode. After the encapsulating step, the cover sheet is stretched directly over and generally along the porous ribbon to form one or more stretch lines.

A device in accordance with the present invention provides for potentiometric analysis of aqueous solutions, such as human biological fluids, wherein the junction time is considerably shorter than that of prior art devices. Shortened junction time has been accomplished by stretching the cover sheet of the device directly over the capillary bridge which provides solution flow. Typically, the stretching is done in such a way so as to mechanically distort the cover sheet in one or more substantially continuous lines, thereby stretching the polymeric material of which the cover sheet is made. It is believed that such stretching allows for further expansion of the wetted porous material, thereby facilitating capillary flow of the liquid samples.

The details of the invention will become more apparent in the detailed description and discussion of the drawings presented hereinbelow.

BRIEF DESCRIPTION OF THE INVENTION

In the detailed description of the invention presented hereinbelow, reference is made to the accompanying drawings in which.

DETAILED DESCRIPTION OF THE INVENTION

Although the invention as described hereinafter is directed to a device for potentiometrically determining ion activity through the use of ion-selective electrodes, such device can also be used for other electrical tests of liquid samples. It is particularly useful for analysis of ionic activity in biological fluids, such as blood serum and urine. The device is particularly adapted for processing by automated handling equipment, such as that described, for example, in commonly assigned U.S. Pat. No. 4,296,070 (issued Oct. 20, 1981 to Montalto et al).

Figure 1:
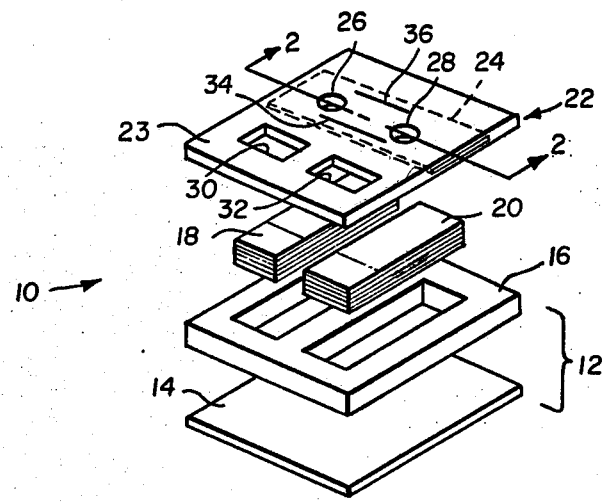
FIG. 1 is an exploded perspective view of a device for determining the activity of an ionic analyte of a liquid, such device constructed according to the present invention.
Figure 2:
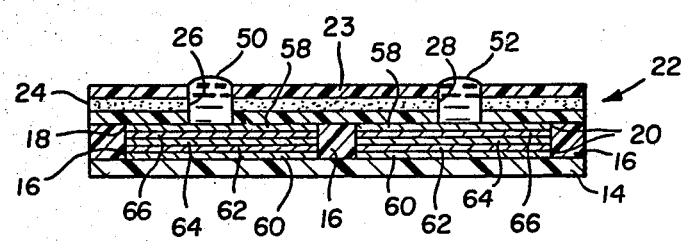
FIG. 2 is an assembled exaggerated sectional view taken generally along the line designated as 2—2 in FIG. 1, and showing liquid drops applied to the device.
Figure 3:
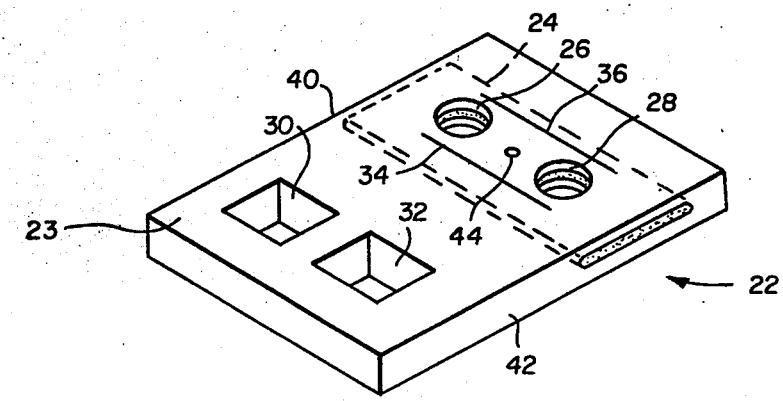
FIG. 3 is a perspective view of a cover sheet element which is a portion of the device illustrated in FIG. 1.

Referring to FIGS. 1-3, a device 10 has an electrically insulative frame 12 comprising an electrically insulative base 14 and a spacer 16 for receiving electrodes. Although of insignificant magnitude to show in the drawings spacer 16 is typically thinner than the electrodes so that the electrodes extend beyond the surface of spacer 16. Two solid electrodes 18 and 20 are mounted in frame 12 in a spaced-apart (i.e. electrically isolated) relationship. Device 10 also includes cover sheet element 22 which is described in more detail hereinbelow.

Electrode pair 18 and 20 can be either (1) an ion-selective electrode and an external reference electrode, for direct mode of determining potentials, or (2) two ion-selective electrodes, for a differential measurement comparing the ion activity of an unknown test liquid with that of a similar reference liquid of known ion concentration. Referring to FIG. 2, electrodes 18 and 20 are shown as being identical and, therefore, suitable for the differential mode of measurement which is typically made with an electrometer when a test drop 50 of a test liquid is deposited into liquid access hole 26 and contacts electrode 18, and a reference drop 52 of a reference liquid is deposited into liquid access hole 28 and contacts electrode 20.

In FIG. 2, the thickness of the electrode layers have been greatly exaggerated for clarity. Both electrodes are formed of layers comprising an ion-selective membrane 58 which is selectively permeable to the ion of choice. Membrane 58 is coated over a multilayer internal reference element which in turn is coated over an electrode support 60, all of which are solid layers. Each internal reference element is shown as comprising several layers including metal layer 62, layer 64 which is composed of an insoluble salt of the metal of layer 62, and layer 66 which contains an electrolyte. Although such layers are generally referred to as being "coated" one over another, it should be understood that the term "coating" is meant to include laminating or otherwise forming the various strata one over another by any technique.

A more detailed description of the electrodes useful in the device of this invention can be found in various references including, for example, commonly assigned U.S. Pat. No. 4,053,381 (issued Oct. 11, 1977 to Hamblen et al), the disclosure of which is incorporated herein by reference.

Referring to FIG. 3, a cover sheet element 22 of this invention is a flat composite article having a pair of liquid access holes 26 and 28, and preferably, a pair of electrical access holes 30 and 32. Element 22 also comprises nonporous cover sheet 23. Useful nonporous materials from which cover sheet 23 can be made include polymeric materials such as polyolefins (e.g. polyethylene, polypropylene, copolymers of olefins, etc.), polystyrenes, polyesters (e.g. polyethylene terephthalate, etc.), polycarbonates and the like. It is important for reasons discussed hereinbelow that the nonporous material of which the cover sheet is somewhat deformable when external force is applied, i.e. it can be stretched or otherwise deformed when subjected to a mechanical deformation process, e.g. embossing. Although this invention is not limited to such, some deformable polymeric materials useful in the practice of this invention are elastic, i.e. they will tend to return to their original shape after deformation over a period of time.

A porous material is encapsulated in cover sheet 23 to form a capillary bridge 24 extending at least between liquid access holes 26 and 28 as a means of promoting ion migration between electrodes 18 and 20 (FIG. 1). Although this capillary bridge can be of any convenient shape (square, trapezoidal, etc.), preferably it is a rectangular or elongated ribbon which extends, in its larger dimension, in a direction of the common centerline of the liquid access holes 26 and 28 and at least between those holes. Preferably, the ribbon extends substantially the entire distance between opposed edges (i.e. the side edges 40 and 42 of cover sheet 23. As used in this specification and in the claims, the porous material used to make the capillary bridge 24 is referred to as a ribbon, which is intended to define any elongated form such as, for example, a web, thread, strip, etc. Generally, the shape, size and thickness of the porous material is optimized to reduce junction time and to have minimal fluid capacity.

In a preferred embodiment of this invention, the porous material is a porous cellulosic paper. A suitable cellulosic paper for absorption of aqueous solutions, such as human serum, is Whatman #2 chroma, 0.007 inch (0.018 cm.) thick, which is manufactured in the United Kingdom by W. & R. Balston, Ltd. When a device containing this paper is spotted with drops of an aqueous solution at holes 26 and 28, the drops fill the holes, forming large caps on cover sheet element 22 (see FIG. 2). Generally, within less than about 60 seconds the liquid is absorbed into the paper. The liquid from each drop spreads into capillary bridge 24 until contact is made at about midway between the liquid access holes to form an ionic junction. Preferably, sufficient liquid is left unabsorbed to fill liquid access holes 26 and 28.

Other suitable porous materials besides paper can be used in the practice of this invention. Another example of such a material is described in U.S. Pat. No. 4,053,381, noted hereinabove. Other porous materials which are resistant to becoming clogged by the nonporous materials used to encapsulate it will readily occur to those skilled in the art.

It is desirable to vent the cover sheet element to promote rapid juncture formation. Vents, such as that represented by numeral 44 in FIG. 3, allow air trapped in the porous material to escape and be displaced by the advancing liquid wave fronts from the liquid access holes. Venting can be accomplished preferably by puncturing cover sheet 23 on its topside (defined as the side into which liquid is dropped into the holes) to expose the porous material to the atmosphere. More preferably, vents should be spaced along the entire bridge area over the porous material between the liquid access holes.

The devices of this invention provide the above-noted advantage of reduced junction time due to one or more, and preferably a plurality, of stretch lines (two being shown in FIG. 1 represented by numerals 34 and 36) provided in the cover sheet of the devices. These lines extend generally along the common centerline of the liquid access holes in spaced relationship with such centerline. Typically, the lines also extend generally in the directionality of the capillary bridge. For instance, in the preferred embodiment of this invention, the capillary bridge is rectangular and extends substantially between opposing sides of the cover sheet. In this embodiment, the stretch lines extend generally in the direction of the larger dimension of the capillary bridge. Although it is not essential, it is preferred that these stretch lines be generally parallel to the common centerline of the liquid access holes. As used throughout this specification and in the claims, the term "generally parallel" meant to encompass a first situation where the stretch lines are parallel to the common centerline and a second situation where the stretch lines, if extended, would intersect with the common centerline at an angle of less than about 45°. More preferably, the stretch lines, if extended, would intersect with the common centerline at an angle of less than about 30°.

A "stretch line," as used in this specification and in the claims, is a narrow region of deformation in the outer surface of the cover sheet element. It could also be defined as an indentation or crease in the surface of the cover sheet element. This deformation in the cover sheet element stretches the nonporous material of which the element is made. The region of stretching is substantially continuous, thereby forming a line. As used throughout this specification and in the claims, the term "substantially continuous" is meant to include stretch lines which have insubstantial or no interruptions. Where there are interruptions, they are very short and far apart in a given stretch line. Preferably each stretch line has a length which is at least equal to the distance between the liquid access holes. Preferably, the stretch line length is greater than the distance between the holes, and less than the sum of the distance between the holes plus the diameter of each hole. The stretch lines can be linear or curvilinear.

Figure 4A:
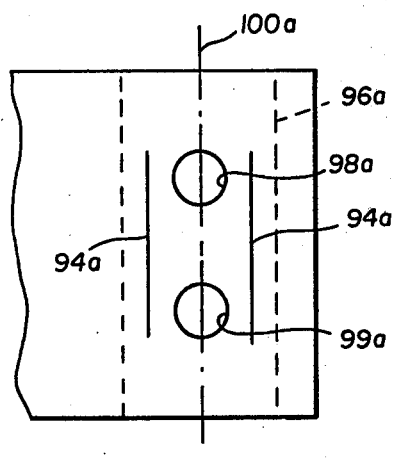
FIGS. 4a-4h are partial plan views of cover sheet elements illustrating various embodiments of stretch lines.
Figure 4B:
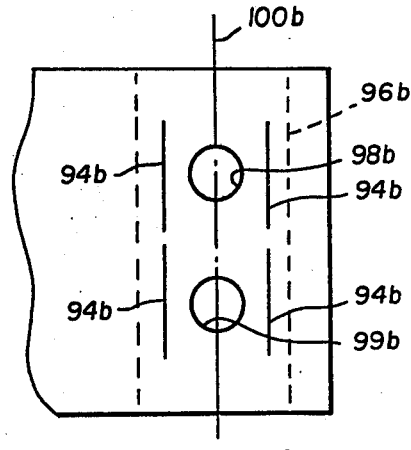
Figure 4C:
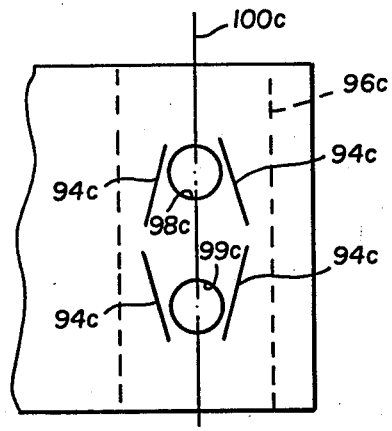
Figure 4D:
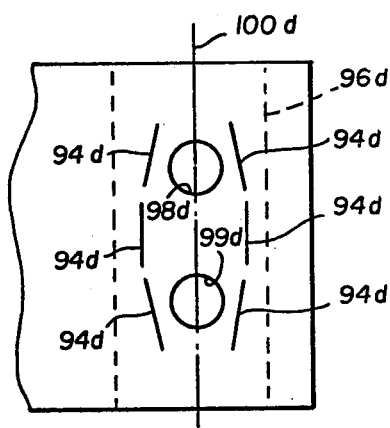
Figure 4E:
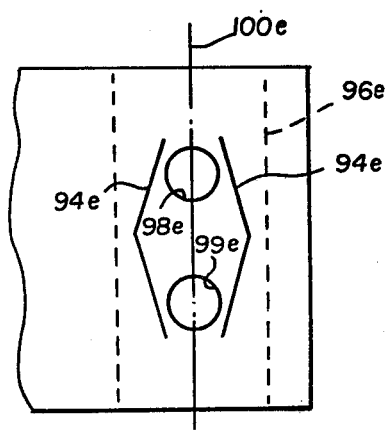
Figure 4F:
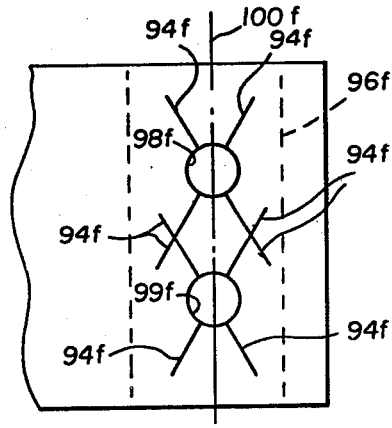
Figure 4G:
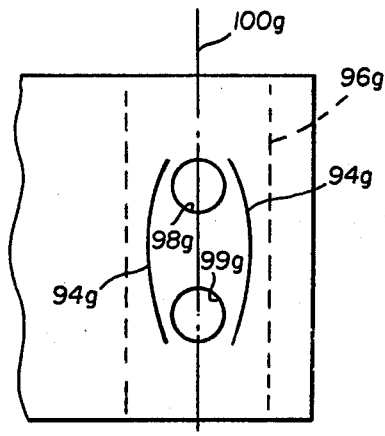
Figure 4H:
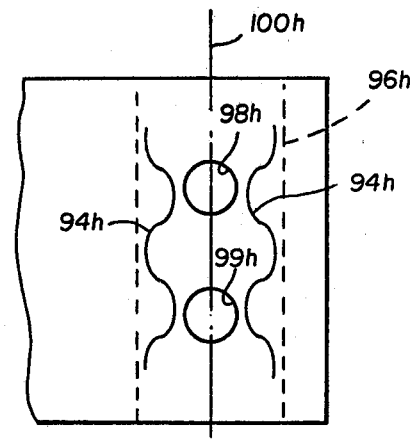

FIGS. 4a–4h illustrate several embodiments of this invention wherein two or more stretch lines in each cover sheet element are represented in various lengths and orientations by numerals 94a–h. The stretch lines lie over capillary bridges 96a–h near liquid access holes 98a–h and 99a–h. The stretch lines lie generally along, or generally extend, in the directionality of the respective common centerlines, represented with numerals 100a–h. These embodiments are meant to be representative only and not limiting as far as possible embodiments of this invention. A preferred embodiment of this invention is illustrated in FIG. 4e wherein the cover sheet has two stretch lines which are not parallel to the common centerline, but are vee shaped and which, if extended, would intersect it at an angle of less than about 45°.

Figure 5:
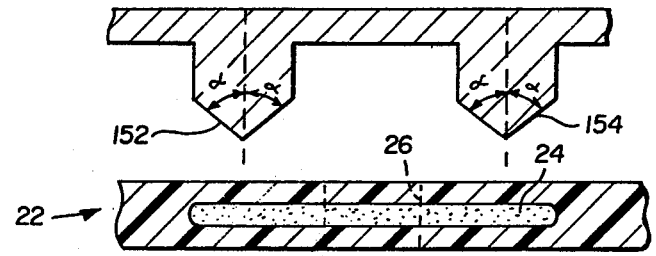
FIG. 5 is an exaggerated, partial sectional view of the cover sheet element of FIG. 3 and an embossing tool useful in preparing the devices of this invention.

The stretch lines can be formed in any suitable manner. Preferably, they are formed by embossing the cover sheet with a suitable tool, such as a rotating wheel having embossing dies (not illustrated) or a punch 150 (FIG. 5) having the appropriate (at least one, and preferably two) number of embossing dies. A typical embossing punch is illustrated in FIG. 5 in relation to a section of a cover sheet element. Punch 150 has two vee edged dies 152 and 154 which are brought down onto a surface of cover sheet element 22 with appropriate force to adequately stretch the cover sheet without cutting through it into the capillary bridge. Dies 152 and 154 typically have an internal angle from vertical referenced as angle $\alpha$ in FIG. 5 of greater than about 30°, and preferably from about 30° to about 75°. The dies can be situated a suitable distance from each other and at appropriate orientations in order to produce the pattern of stretch lines desired directly over capillary bridge 24 and near liquid access hole 26. Some of the stretch line patterns are illustrated in FIGS. 4a–4h. In addition to using a mechanical deformation device, ultrasonic or other wave energy can be applied to the cover sheet in the area of the deformation to enhance the stretching, if desired.

Figure 6A:
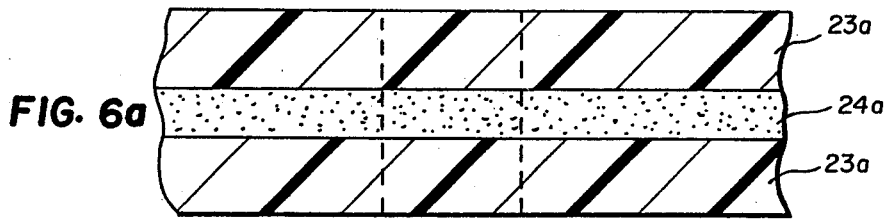
FIGS. 6a-6b are exaggerated, partial sectional views of cover sheet elements like those illustrated in FIG. 3a, with and without stretch lines.
Figure 6B:
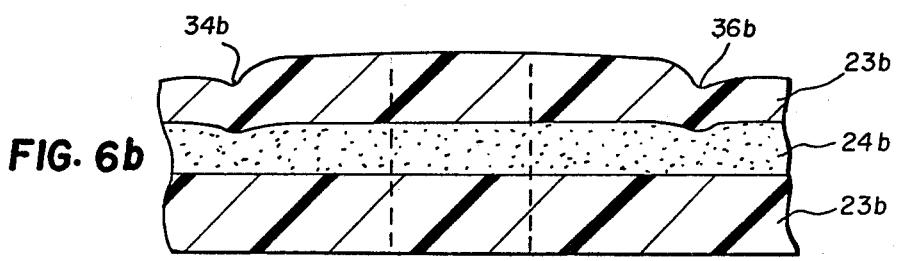

Referring to FIGS. 6a and 6b, the cover sheet element of FIG. 6a, having cover sheet 23a and capillary bridge 24a, is subjected to deformation with a suitable embossing tool using suitable force, and is transformed into the cover sheet element of FIG. 6b. This cover sheet element comprises cover sheet 23b, capillary bridge 24b and stretch lines 34b and 36b. Both of these illustrations are highly exaggerated for clarity in describing this invention.

Without being bound to any particular theory, it is believed that the formation of the stretch lines in the cover sheet as illustrated in FIG. 6b lengthens the upper cover sheet surface enough to allow the highly-compressed capillary bridge encapsulated therein to expand. This expansion enlarges the free space within the bridge, thereby allowing faster liquid flow therein. As a result, junction time is reduced when liquids are introduced into the liquid access holes.

The assembled devices of this invention can be prepared in any number of ways. A preferred assembly method (excluding the formation of the stretch lines) is described in U.S. Pat. No. 4,336,091, noted hereinabove, the disclosure of which is incorporated herein by reference. Generally, in this preferred method of assembly, all of the materials except the ion-selective electrodes are assembled by simply laminating continuous webs of material together and chopping finished devices from the resulting composite web.

The cover sheet can be embossed or otherwise treated to form the stretch lines at any suitable point of device assembly after the encapsulation of the porous material in the cover sheet. Preferably, this stretching occurs after the frame is joined to the nonporous cover sheet element web with the electrodes therebetween. Stretching could occur immediately before, after or at the same time the composite web is severed into individual devices. Preferably, it occurs simultaneous to the time the composite web is severed, such as at knife press (represented as numeral 130 in U.S. Pat. No. 4,336,091 noted hereinabove).

The invention has been described in detail with particular reference to preferred embodiments thereof, but it will be understood that variations and modifications can be effected within the spirit and scope of the invention.

I claim:

1. A method of making a device for determining the ionic analyte activity in a contacting sample of a liquid, said method comprising the steps of:

encapsulating a ribbon of porous material in a nonporous cover sheet to form a cover sheet element;

applying a pair of solid electrodes in a spaced-apart relationship to an electrically insulative frame member;

forming a pair of liquid access holes in said cover sheet element through said porous material, said liquid access holes having a common centerline;

joining said cover sheet element to said frame member with said electrodes therebetween in an orientation such that each of said liquid access hole is aligned with a different electrode; and after said encapsulating step, using an embossing tool to stretch said cover sheet directly over and generally along said porous ribbon to form at least one substantially continuous stretch line.

2. The method of claim 1 wherein said embossing tool comprises two or more embossing dies each having a vee edge with an integral angle greater than about 30°.

3. The method of claim 2 wherein said embossing dies have a length at least equal to the distance between said liquid access holes and are substantially parallel to said common centerline of said liquid access holes.

* * * * *